US00PP11847P2

(12) United States Plant Patent
Leue

(10) Patent No.: US PP11,847 P2
(45) Date of Patent: Apr. 24, 2001

(54) DOUBLE IMPATIENS PLANT NAMED 'BALFIEORCE'

(75) Inventor: Ellen F. Leue, Dekalb, IL (US)

(73) Assignee: Ball FloraPlant, a division of Ball Horticultural Company

( * ) Notice: Subject to any disclaimer, the term of this patent is extended or adjusted under 35 U.S.C. 154(b) by 0 days.

(21) Appl. No.: 09/475,997

(22) Filed: Dec. 31, 1999

(51) Int. Cl.[7] ..... A01H 5/00
(52) U.S. Cl. ..... Plt./317
(58) Field of Search ..... Plt./317

*Primary Examiner*—Bruce R. Campell
*Assistant Examiner*—Annette H Para
(74) *Attorney, Agent, or Firm*—C. A. Whealy

(57) ABSTRACT

A new and distinct cultivar of Double Impatiens plant named 'Balfieorce', characterized by its numerous fully double orange-colored flowers; upright and mounded plant habit; and freely basal-branching habit.

1 Drawing Sheet

BACKGROUND OF THE INVENTION

The present invention relates to a new and distinct cultivar of Double Impatiens plant, botanically known as *Impatiens walleriana*, and hereinafter referred to by the cultivar name 'Balfieorce'.

The new Impatiens is a product of a planned breeding program conducted by the Inventor in Elburn, Ill. The objective of the breeding program was to develop new Double Impatiens cultivars with freely-branching vigorous growth habit, numerous large fully double flowers, and attractive flower and foliage colors.

The new Impatiens originated from a cross made by the Inventor of the proprietary selection of *Impatiens walleriana* identified as code number 0043-4-1-3-1-1 as the male, or pollen parent, with the proprietary selection of *Impatiens walleriana* identified as code number 487c-2-1 as the female, or seed parent. The cultivar 'Balfieorce' was discovered and selected by the Inventor as a flowering plant within the progeny of the stated cross in a controlled environment in Elburn in 1996.

Asexual reproduction of the new cultivar by terminal cuttings taken at Elburn, Ill., has shown that the unique features of this new Impatiens are stable and reproduced true to type in successive generations of asexual reproduction.

SUMMARY OF THE INVENTION

The following traits have been repeatedly observed and are determined to be the unique characteristics of 'Balfieorce'. These characteristics in combination distinguish 'Balfieorce' as a new and distinct cultivar:

1. Numerous fully double orange-colored flowers.
2. Upright and mounded plant habit.
3. Freely basal-branching habit.

The new Impatiens can be compared to the cultivar, Rosebud Orange, not patented. However, in side-by-side comparisons conducted by the Inventor in Elburn, plants of the new Impatiens differ from plants of the cultivar Rosebud Orange in the following characteristics:

1. Plants of the new Impatiens are larger than plants of the cultivar Rosebud Orange.
2. Plants of the new Impatiens have longer peduncles than plants of the cultivar Rosebud Orange. Flowers of plants of the new Impatiens are positioned just above the foliage whereas flowers of plants of the cultivar Rosebud Orange are positioned within the foliage.
3. Plants of the new Impatiens and the cultivar Rosebud Orange differ in flower color.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which more accurately describe the actual colors of the new Impatiens. The photograph comprises a top perspective view of a typical flowering plant of 'Balfieorce'.

DETAILED BOTANICAL DESCRIPTION

The cultivar Balfieorce has not been observed under all possible environmental conditions. The phenotype may vary somewhat with variations in environment such as temperature and light intensity, without, however, any variance in genotype. The following observations and measurements describe plants about 10 weeks after planting rooted cutting and grown in 10-cm pots in West Chicago, Ill. under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Impatiens walleriana* cultivar 'Balfieorce'.

Parentage:

*Male parent.*—Proprietary selection of *Impatiens walleriana* identified as code number 0043-4-1-3-1-1, not patented.

*Female parent.*—Proprietary selection of *Impatiens walleriana* identified as code number 487c-2-1, not patented.

Propagation:

*Type cutting.*—Terminal cuttings.

*Time to initiate roots.*—About 7 days with 18° C.

*Time to develop roots.*—About 21 days with 18° C.

*Rooting habit.*—Fibrous, fine, freely branching.

Plant description:

*Plant form.*—Upright and mounded.

*Growth and branching habit.*—Moderately vigorous. Freely basal-branching with about three lateral branches at the base, dense and bushy growth. Appropriate for 10 and 12.5-cm containers.

*Crop time.*—About 5 to 7 weeks are required to produce finished flowering plants from rooted cuttings in a 10-cm container.

*Plant height.*—About 12.8 cm.

*Lateral branches.*—Diameter: About 8.8 mm. Internode length: About 3 cm. Color: 146D with streaks of 183C, streaks predominately at nodes.

*Foliage description.*—Leaves simple, generally symmetrical, abundant, alternate. Length: About 4.9 cm. Width: About 3.1 cm. Shape: Ovate. Apex: Acuminate. Base: Attenuate. Margin: Crenate with ciliation. Texture: Smooth, glabrous. Color: Fully expanded foliage, upper surface: Close to 137A. Fully expanded foliage, lower surface: Close to 137C. Venation, both surfaces: 144A. Petiole: Length: About 1.7 cm. Diameter: About 2 mm. Color: 147C with streaks of 138C near stem.

Flower description:

*Flower type and habit.*—Numerous and consistently double orange-colored flowers. Flower buds open similar to a rose in fullness. Freely and continuously flowering. Flowers arise from leaf axils. Usually about 10 flowers and flower buds per lateral branch and about 30 flowers and flower buds per plant. Flowers positioned above the foliage and typically face outward and upright. Flowers not persistent.

*Flowering season.*—Year-round under greenhouse conditions. In the garden, flowering is continuous from spring until fall.

*Flower size.*—Diameter: About 4.3 cm. Depth (height): About 3 cm.

*Flower buds.*—Length: About 1.6 cm. Diameter: About 1 cm. Shape: Ovoid. Color: 40D.

*Petals.*—Quantity/arrangement: About 27 per flower; imbricate. Length: About 2.5 cm. Width: 2.1 cm. Shape: Obovate. Apex: Rounded to emarginate. Base: Attenuate. Margin: Entire. Texture: Smooth, iridescent. Color: When opening, upper surface: Darker than 32A. Fully opened, upper surface: Close to 32A; color fading to 34A with subsequent development. Fully opened, lower surface: Between 41C and 41D.

*Peduncles.*—Length: About 3.2 cm. Angle: Upright or outward. Strength: Moderately strong. Color: 146D.

*Reproductive organs.*—None observed.

Disease resistance: Under commercial conditions, resistance to pathogens common to Double Impatiens has not been observed.

Seed development: Seed production has not been observed.

It is claimed:

1. A new and distinct cultivar of Double Impatiens plant named 'Balfieorce', as illustrated and described.

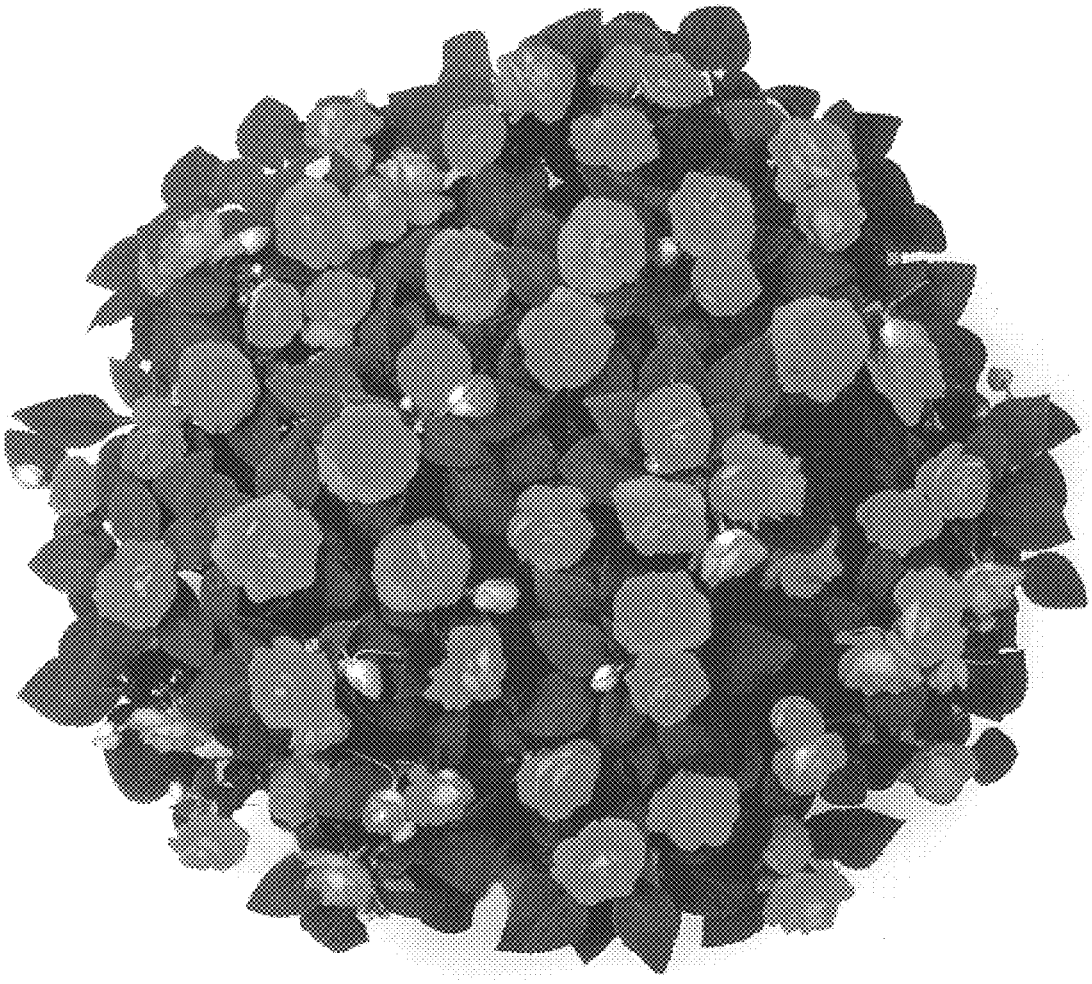

* * * * *